US00PP28935P2

(12) United States Plant Patent
Vinson et al.

(10) Patent No.: US PP28,935 P2
(45) Date of Patent: Feb. 6, 2018

(54) ***FRAGARIA* PLANT NAMED 'SWV 25'**

(50) Latin Name: *Fragaria×ananassa*
Varietal Denomination: SWV 25

(71) Applicants: Peter Edward Vinson, Kent (GB); Ilona Eva McCarthy, Kent (GB); Simon Peter Warren, Faversham (GB)

(72) Inventors: Peter Edward Vinson, Kent (GB); Ilona Eva McCarthy, Kent (GB); Simon Peter Warren, Faversham (GB)

(73) Assignee: EDWARD VINSON LTD., Faversham (GB)

( * ) Notice: Subject to any disclaimer, the term of this patent is extended or adjusted under 35 U.S.C. 154(b) by 0 days.

(21) Appl. No.: 15/330,399

(22) Filed: Sep. 15, 2016

(51) Int. Cl.
*A01H 5/08* (2006.01)

(52) U.S. Cl.
USPC ..... Plt./208

(58) Field of Classification Search
USPC ..... Plt./208
See application file for complete search history.

*Primary Examiner* — Annette H Para
(74) *Attorney, Agent, or Firm* — Penny J. Aguirre

(57) ABSTRACT

A new and distinct short day Mediterranean cultivar of strawberry plant named 'SWV 25' that is characterized by its early to mid-season berry crop, its compact and semi-upright plant habit, its moderate growth rate, berries that are medium red in color, conical in shape, uniform and medium to large in size, its berries with skin that is very firm with a highly glossy surface in texture and firm flesh with resistance to bruising, its fruit that is low in acid with a consistent level of sugars and an excellent eating quality, and its high fruit yield.

2 Drawing Sheets

Botanical classification: *Fragaria×ananassa.*
Variety denomination: 'SWV 25'.

BACKGROUND OF THE INVENTION

The present invention relates to a new and distinct cultivar of *Fragaria*, botanically known as *Fragaria×ananassa* 'SWV 25', and will be referred to hereafter by its cultivar name, 'SWV 25'. 'SWV 25' is a Mediterranean short day strawberry, primarily adapted to the climate and growing conditions of the Mediterranean and other regions of similar climate and day length.

The new cultivar of *Fragaria* is a selection from a controlled breeding program conducted by the Inventors in a glass greenhouse. The objectives of the breeding program are to create new *Fragaria* cultivars with high fruit yields with fruit that are large, uniform, have firm skin, pleasant taste, and low acid content combined with consistent production and a high disease tolerance.

'SWV 25' was derived from a cross made in 2011 under controlled conditions between unnamed and unpatented plants of *Fragaria×ananassa* from the Inventor's breeding program in Faversham, Kent, United Kingdom; reference no. 'SVF 72', as the female parent and reference no. 'S06WL48', as the male parent. 'SWV 25' was selected as a single unique plant in spring of 2012 from amongst the seedlings that resulted from this cross in Cartaya, Huelva, Spain.

Asexual propagation of the new cultivar was first accomplished by both tissue culture using meristematic tissue and rooting of stolons in Faversham, Kent, United Kingdom in 2012 under the direction of the Inventors. Asexual propagation by rooting of stolons and tissue culture has shown that the unique characteristics of the new cultivar are stable and reproduced true to type in successive generations.

BRIEF SUMMARY OF THE INVENTION

The following traits have been repeatedly observed and represent the characteristics of the new cultivar. These attributes in combination distinguish 'SWV25' as a unique cultivar of *Fragaria.*

1. 'SWV 25' exhibits a short day fruiting habit (Mediterranean type).
2. 'SWV 25' exhibits an early to mid-season berry crop.
3. 'SWV 25' exhibits a compact, semi-upright plant habit.
4. 'SWV 25' exhibits berries that are medium red in color.
5. 'SWV 25' exhibits fruit that is conical in shape, uniform and medium to large in size.
6. 'SWV 25' exhibits berries with skin that is very firm with a highly glossy surface in texture and firm flesh with resistance to bruising.
7. 'SWV 25' exhibits its fruit that is low in acid with a consistent level of sugars and an excellent eating quality.
8. 'SWV 25' exhibits a high fruit yield.

'SVF 72', the female parent of 'SWV 25', differs from 'SWV25' in having a later harvest season, lower fruit yields, berries that are smaller in size with a less intense flavor. 'S06WL48', the male parent of 'SWV 25', differs from 'SWV 25' in having a later harvest season and berries that are smaller in size with more intense flavor and fruit trusses that are complex.

'SWV 25' can be most closely compared to the *Fragaria* cultivars 'Viva Patricia' (U.S. Plant Pat. No. 22,717) and 'Camerosa' (U.S. Plant Pat. No. 8,708). 'Viva Patricia' is similar to 'SWV 25' in being a Mediterranean, short day variety. 'Viva Patricia' differs from 'SWV 25' in having a more upright growth habit, slightly more vigorous growth habit a taller and wider plant size, higher canopy density, leaf margins that are serrated ('SWV 25' margins are crenate), larger leaf size, longer petioles, berries that are rhomboid in shape and orange-red in color and larger in size, a higher fruit yield rate and a later blooming and harvest season. 'Camerosa' is similar to 'SWV 25' in having an earlier blooming and harvest season. 'Camerosa' differs from 'SWV 25' in having a higher fruit yield and berries that have a less desirable fruit shape and larger in size with skin that is less firm.

BRIEF DESCRIPTION OF THE DRAWINGS

The accompanying colored photographs illustrate the overall appearance and distinct characteristics of the new *Fragaria*. The photographs were taken of plants 5 to 6 months (3 months in FIG. 1) in age as grown under tunnels using polyethylene covers in a field trial plot in Cartaya, Spain.

The photograph in FIG. 1 provides a view of the plant habit of 'SWV 25' 3 months after planting.

Figure 1:
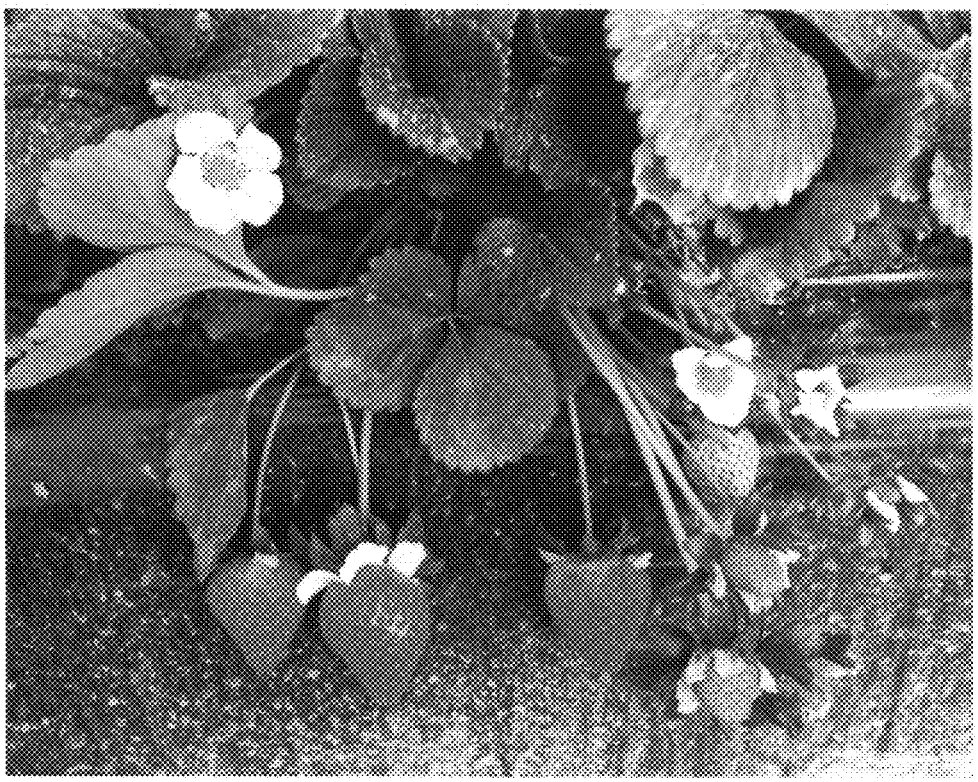
Figure 2:
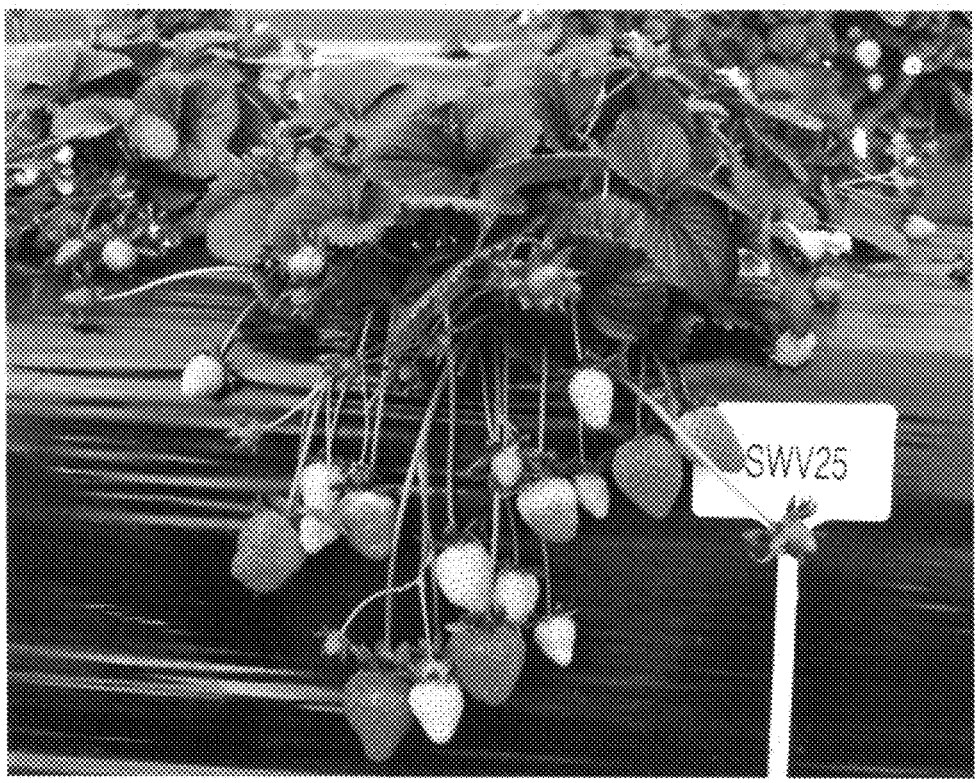

The photograph in FIG. 2 provides a view of the medium-upright plant habit and fruit development stages of 'SWV 25'.

Figure 3:
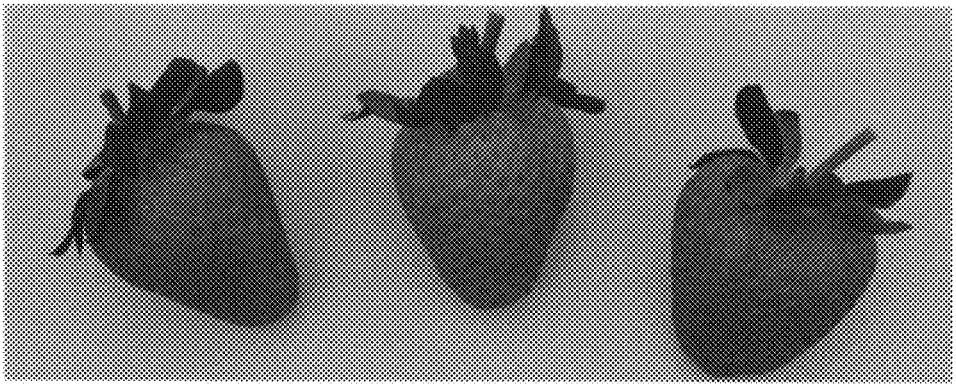

The photograph in FIG. 3 provides a close-up view of the berries of 'SWV 25'.

Figure 4:
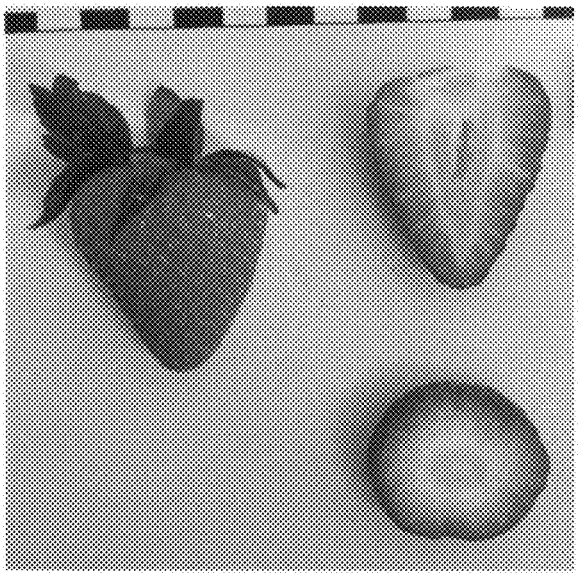

The photograph in FIG. 4 provides a close-up view of the fruit with a whole berry alongside longitudinal and transverse cross sections of 'SWV 25'.

Figure 5:
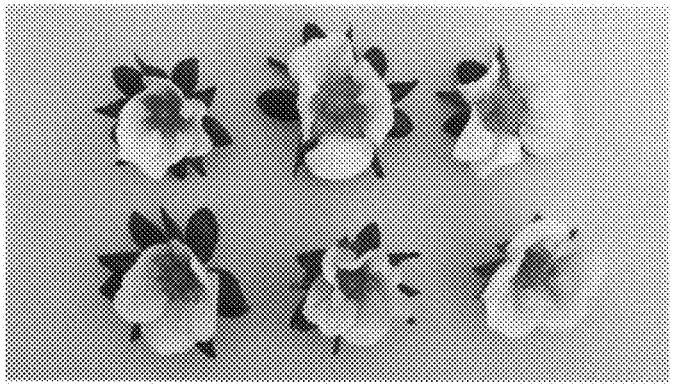

The photograph in FIG. 5 provides a close-up view of the flowers of 'SWV 25'.

The colors in the photographs are as close as possible with the digital photography techniques available and the color values cited in the detailed botanical description accurately describe the colors of the new *Fragaria*.

DETAILED BOTANICAL DESCRIPTION

The following is a detailed description of five to six month-old plants of the new cultivar as grown in trial field plots in 2016 using tunnels and polyethylene covers in Cartaya, Huelva, Spain. The phenotype of the new cultivar may vary with variations in environmental, climatic, and cultural conditions, as it has not been tested under all possible environmental conditions. The color determination is in accordance with The 1995 R.H.S. Colour Chart of The Royal Horticultural Society, London, England, except where general color terms of ordinary dictionary significance are used.

General description:

*Type of bearing.*—Mediterranean, short day.

*Blooming period.*—Early December to end of May in Cartaya, Huelva, Spain.

*Plant type.*—Herbaceous fruit producing perennial.

*Plant habit.*—Upright, medium density canopy.

*Height and spread.*—Medium, reaches an average of 16 cm in height and 30.2 cm in width.

*Cold hardiness.*—Unknown as grown only in temperate climates and not tested in areas where temperatures less than 32° F. occur.

*Diseases.*—No specific tolerances or susceptibilities have been observed.

*Root description*—Fibrous roots, 155B in color.

*Root development.*—Initiated after two weeks and it takes a further three weeks to produce a fully rooted plant.

*Propagation.*—Tissue culture and rooting of stolons.

*Growth rate.*—Moderately vigorous.

*Stem description*—Acaulescent.

Foliage description:

*Leaves per plant.*—An average of 28.

*Leaf division.*—Trifoliate.

*Leaf arrangement.*—Basal.

*Leaf attachment.*—Petiolate.

*Leaflet shape.*—Orbicular.

*Mid-tier leaflet size.*—Average of 67 mm cm in length and 70 mm in width.

*Leaflet margins.*—Crenate, with an average of 22.3 serrations per leaflet and 30.7 mm from petiolule to first serration.

*Leaflet aspect.*—Most leaflets are slightly concave.

*Leaflet interveinal blistering.*—Minimal.

*Leaflet surface.*—Upper surface glossy, lower surface dull, covered with upwards facing hairs, sparse and weak in strength.

*Leaflet color.*—Adaxial surface; 139A, abaxial surface; 139C, with no variegation present on either surface.

*Leaflet venation.*—Upper and lower surfaces; arcuate venation, with vasculature coloration matching the leaf.

*Leaflet glossiness.*—Adaxial is medium and abaxial is low.

*Petiole.*—Round in shape, 13.2 cm in length and 4 mm in width, medium in strength, 144B in color, surface sparsely covered with pubescent hairs.

*Petiolules.*—Round in shape, 7 mm in length and 2 mm in width, medium in strength, 144B in color, surface sparsely covered with pubescent hairs.

*Stipule.*—Average of 3.6 cm in length, 1 cm in width, with a medium to slightly crisp surface texture, 60A to 60B in color on both surfaces.

*Bracts.*—Bract leaflets are infrequent but are observed on a limited number of flower trusses from an early developmental stage.

Flower description:

*Inflorescence.*—Truss.

*Trusses.*—An average of 19.9 cm in length and a 3 mm in width, branching at an average of 7.7 cm from the base.

*Flower initiation and expression conditions.*—Temperature and day length dependent.

*Time of flowering.*—Early in Cartaya, Spain, (50% of plants at first flower).

*Flower position relative to foliage.*—Flowers are generally within the foliage.

*Flower size.*—Average of 3.4 cm in diameter.

*Flower fragrance.*—Medium to strong.

*Calyx.*—Larger than the corolla, average of 3.8 cm in diameter, re-curved.

*Sepals.*—Average of 10 per flower, adaxial surface is 139A in color, abaxial surface is 138A in color, re-curved to horizontal in shape, apex acute to acuminate, base cuneate.

*Petals.*—5, round in shape, margins entire and slightly undulate, apex rounded to slightly acute, base cuneate, 1.6 cm in length and width, slightly overlapping, 155B in color on both surfaces, glabrous surface texture on both surfaces.

*Peduncle.*—Strong in strength, 145A to 145B in color, pubescent surface texture, an average of 10 cm in length and 3.5 mm in width.

*Pedicel.*—Strong in strength, 145A to 145B in color, an average of 8 cm in length and 2.5 mm in width, surface covered with pubescent hairs held horizontally.

*Pistils.*—Numerous, stigma; capitate, 0.5 mm in length, and 11A in color, style; an average of 1.5 mm in length and 145D in color.

*Stamens.*—Average of 25, anthers; elliptic-oblong in shape, 1.4 mm in length, 1.2 mm in width, 13A in color, filaments; 4 mm in length, 145C in color, pollen; moderate in quantity and 4A in color.

Fruit description:

*Time of ripening.*—Early in Huelva, Cartaya, Spain, (50% of plants with first ripe fruit).

*Shape.*—Primarily conical, with minimal differences between primary, secondary and tertiary fruit.

*Size.*—Large to medium; 5.3 cm and 4.4 cm in width.

*Surface.*—Smooth and highly glossy.

*Fruit appearance.*—Symmetrical and attractive.

*Calyx position.*—Even to fruit surface.

*Attitude of calyx segments.*—Most re-curved, strong adherence to the fruit.

*Diameter of calyx relative to fruit diameter.*—Calyx diameter is larger than fruit diameter (Calyx: Fruit=1.34).

*External color* (*skin*).—Very even color, 45A in color, color is retained throughout the cropping season.

*Internal color* (*flesh*).—Near to the skin, 32C in color, near to the center the flesh color is 31C.

*Acidity.*—Low.

*Sweetness.*—Good, with a mean Brix of 8.04% over two seasons (Feb. 13, 2015-Apr. 25, 2015 and Jan. 27, 2016-Apr. 7, 2016).

*Firmness.*—Skin is very firm and resistant to bruising, flesh is moderately firm.

*Aroma.*—Slight.

*Weight*—Mean berry weight of 27.7 g and 989 g per plant in a harvest season (Feb. 13, 2015-Apr. 25, 2015).

*Hollow center.*—Limited to a small number of primary fruit.

*Achene color.*—5A.

*Achene position.*—Even and level with the skin surface.

*Achene number.*—An average of 345 per berry.

*Band within achenes.*—Very narrow.

*Yield.*—An average of 277 g/plant in trials by the first of April in 2016.

It is claimed:

1. A new and distinct cultivar of strawberry plant named 'SWV 25' as herein illustrated and described.

* * * * *